United States Patent [19]

Bell

[11] Patent Number: 5,088,441
[45] Date of Patent: Feb. 18, 1992

[54] CORD IMPREGNATOR
[75] Inventor: Joseph V. Bell, Santa Barbara, Calif.
[73] Assignee: Belport Co., Inc., Camarillo, Calif.
[21] Appl. No.: 571,218
[22] Filed: Aug. 23, 1990
[51] Int. Cl.[5] .................. B05C 3/172; B05C 11/02
[52] U.S. Cl. ......................... 118/67; 28/180;
28/183; 118/117; 118/405; 118/420; 118/DIG. 19; 118/DIG. 20
[58] Field of Search .................. 118/67, 68, 118, 119,
118/234, 235, 405, 420, DIG. 19, DIG. 20, 117;
28/179, 180, 183

[56] References Cited
U.S. PATENT DOCUMENTS

| 397,539 | 2/1889 | Dahlgren | 28/179 X |
| 1,949,237 | 2/1934 | Bradner | 118/405 X |
| 2,547,047 | 4/1951 | Saums et al. | 118/420 |
| 2,851,763 | 9/1958 | Adams | 28/183 |

Primary Examiner—Michael Wityshyn
Attorney, Agent, or Firm—Jack C. Munro

[57] ABSTRACT

The method of impregnating and the apparatus for impregnating a thin cord with a medicinal solution with the cord to be used in the dental field as an appliance for gingival retraction in conjunction with the teeth of a human being. The cord is immersed in a bath of the medicinal solution, moved from the bath to a squeezing roller assembly so that the medicinal solution evenly permeates the cord, removing excess solution, drying the cord and winding the cord on a wind-up reel prior to being dispensed to the consumer.

3 Claims, 1 Drawing Sheet

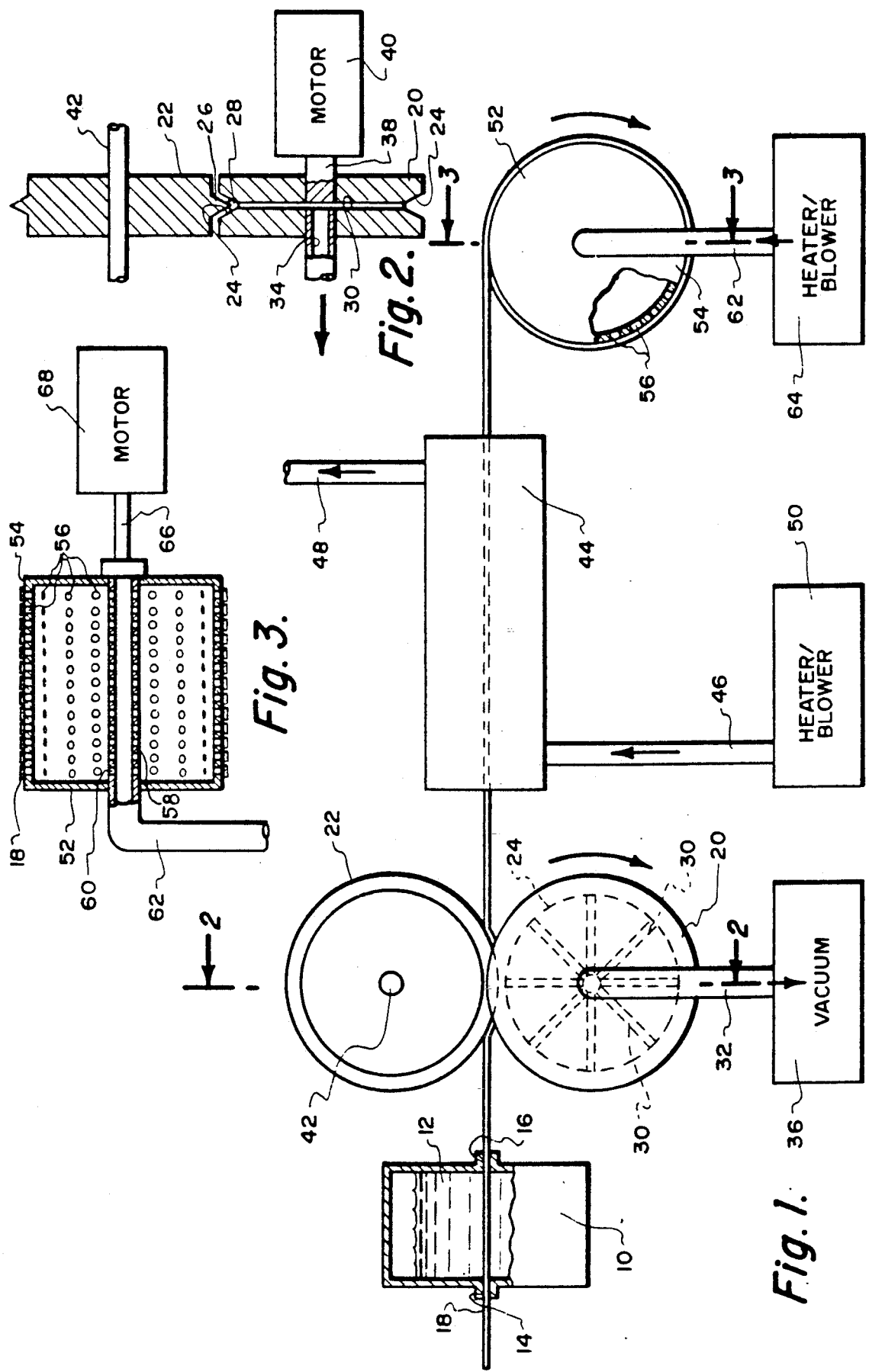

_5,088,441_

CORD IMPREGNATOR

BACKGROUND OF THE INVENTION

The field of this invention relates to dental equipment and more particularly to an appliance which is to be used by a dentist to assist in the performing of certain dental procedures.

The use of a gingival retraction cord has long been known in the dental field. A typical gingival retraction cord is about one-eighth of an inch in diameter, is similar to a conventional string and is utilized by the dentist by being wrapped around the base of a tooth located within the alveolar. It is common for the cord to contain some type of a medicament and/or astringent. As the cord is left temporarily on the tooth, the medicament and/or astringent is released from the cord and applied directly to the gum area adjacent to the tooth. Typically, these types of cords are applied to retract the gingival so as to make it easier for the dentist to perform certain procedures such as installing crowns or bridges. Also, such cords can be a big help in assisting of healing of the gingival.

In the past, it has been common to make cord in a large quantity, immerse it in a quantity of the liquid medicament, remove the cord from the liquid medicament, dry the cord, divide the cord into desired lengths which are then to be placed within an appropriate container to be sold to the dentist.

Some people are sensitive to certain medication and if a greater amount of medication is applied to that particular individual, that individual could have an undesirable reaction. The immersing of a gingival retraction cord in a medicinal solution has not been closely controlled so as to avoid any undesirable reaction. There has always been, in a given length of cord, some areas of diminished amount of medicine and other areas of significantly increased amounts of medicine. Precise impregnation to achieve even distribution of the medicine throughout the cord has just not been obtainable in the prior art.

There is a need to construct a device which will impregnate a cord with a medicinal solution with this impregnation being substantially even throughout the entire length of the cord so that some areas of the cord will not have significantly increased amounts of medication and other areas of the cord have diminished amounts of medication.

SUMMARY OF THE INVENTION

A method of impregnating a cord with a medicinal solution which involves immersing of a length of cord within a bath of the medicinal solution, removing the cord from the bath and placing it in conjunction with a squeezing apparatus to physically squeeze the cord, moving the cord from the squeezing apparatus in conjunction with a drying apparatus and then winding the cord on a wind-up drum. The method of the present invention is deemed to be inventive by utilizing of a vacuum in conjunction with the squeezing apparatus so as to extract excess medicinal solution which greatly assists achieving of even distribution of the medicinal solution throughout the length of the cord. Also the incorporating of a second drying apparatus in conjunction with the wind-up drum is also deemed to be inventive.

The primary objective of the present invention is to construct an apparatus for making and a method for making of a string-like cord that is impregnated with a medicinal solution with the quantity of impregnation being substantially constant throughout the entire length of the cord.

Another objective of the present invention is to construct an apparatus which minimizes manufacturing cost of the cord.

BRIEF DESCRIPTION OF THE DRAWING

FIG. 1 is a schematic view of the apparatus that is utilized to achieve the method of the present invention;

FIG. 2 is a cross-sectional view through the squeezing apparatus utilized in conjunction with the apparatus of the present invention taken along line 2—2 of FIG. 1; and FIG. 3 is a cross-sectional view through the wind-up drum utilized in conjunction with the apparatus of the present invention taken along line 3—3 of FIG. 1.

DETAILED DESCRIPTION OF THE SHOWN EMBODIMENT

Referring particularly to the drawing, there is shown, generally, in FIG. 1 a container 10 which contains a quantity of a desired medicinal solution 12. It is to be understood that the composition of the medicinal solution 12 can be readily varied. It is to be selected according to what particular medicine is utilized to impregnate the cord 18. The cord 18 is conducted from a source (not shown) through an entry opening 14 into the container 10. From the container 10 the cord 18 is extracted through an exit opening 16.

From the exit opening 16, the cord 18 is moved into conjunction with a V-shaped groove 24 of a first squeezing wheel 20. Squeezing wheel 20 is rotatable as depicted by the arrow shown directly adjacent the periphery of the wheel 20 in FIG. 1 with this rotation to occur by means of a shaft 38 which is rotatably driven by an electrically operated motor 40. Extending within a portion of the groove 24 is a substantially mating tongue 26 of a second wheel 22. This wheel 22 is mounted on a shaft 42 with shaft 42 functioning only as an idler shaft. As the cord 18 passes through the area located between the tongue 26 and the groove 24, the cord 18 is squeezed assuming a different configuration depicted by numeral 28.

During the squeezing operation, excess medicinal liquid is extracted from the cord 28 and this medicinal liquid is caused to flow into any one of a plurality of spoke-like conduits 30 formed within the wheel 20. These conduits 30 all connect at the central axis to a main extraction conduit 34 which is formed within a tube 32. A vacuum source 36 applies a vacuum within the tube 34 which functions to move the excess medicinal liquid from the cord 28 into the conduits 30 and into the main collection conduit 34 and to a collecting container (not shown) which is located in conjunction with the vacuum source 36.

After passing between the rollers 20 and 22, the cord 18 resumes its former shape and is conducted within an elongated drying chamber 44. The elongated drying chamber 44 is substantially closed with the exception of a small inlet opening (not shown) for the cord 18, a small outlet opening (not shown) for the cord 18, for heated air inlet tube 46 and heated air outlet tube 48. Heated air inlet tube 46 is to receive heated air from a heater blower 50 with such heater blowers being deemed to be conventional and forming no specific part of this invention. The common type of a structure for a heater blower 50 would be an electrically driven fan which works in conjunction with a heating coil. An extremely simplified version of such a heater blower 50 would be what is conventionally available to the consumer as a conventional hair dryer.

The heated air from the heater blower 50 is caused to be continuously subjected tot he cord 18 as it is conducted through the drying chamber 44. It is to be noted that the inlet conduit 46 is mounted at one end of the chamber 44 with the outlet conduit 48 being mounted at the opposite end. Generally, the outlet conduit 48 will merely be open to the ambient.

The cord 18 from the drying chamber 44 is now to be wound on a wind-up drum 52. This drum 52 has an exterior surface 54 on which the cord 18 is to be directly wound. This exterior surface 54 includes a mass of tiny holes 56. The drum 52 is to e rotatably driven by a motor 68 through a shaft 66. The rotation of the motor 68 is to be synchronized with the motor 40 so that there is little or no tension on the cord 18 from the squeezing rollers 20 and 22 to the wind-up drum 52. This is so that the cord 18 will be would on the drum 52 in a nonstretched position. It is to be understood that once a selected quantity of the cord 18 is wound on the drum 52, this cord will be removed from the drum 52 with selected quantities being removed from the enlarged quantity located on the drum 52. It is the selected quantities that will be sold to the ultimate consumers.

Centrally mounted in conjunction with the drum 52 is a tube 58. Tube 58 includes a mass of holes 60 formed within the side wall. Tube 58 connects with a conduit 62. Conduit 62 connects with a heater blower apparatus 64 which is essentially identical to apparatus 50. Heated air from the heater blower 64 is conducted through conduit 62 into tube 58, through holes 60 and through holes 56 to be passed over the cord 18 as it is being wound on the drum 52. The usage of the heater blower 64 further insures that the cord 18, as it is wound on the drum 52, is dry as possible.

It is important to install within the patient a dry cord and after installation, due to mouth rinses and saliva, the cord will become damp and at that time will release the medicinal solution. If the cord is wet prior to being installed within the mouth of the user, the cord will be releasing the medicinal solution where it is not needed and therefore the overall effectiveness of the cord will be substantially decreased.

What is claimed is:

1. A cord impregnator comprising:
   a length of thin cord;
   a bath containing a liquid medium, said cord being immersed in said liquid medium;
   a powered squeezing roller assembly, said squeezing roller assembly comprising a first wheel and a second wheel, said first wheel having a V-shaped continuous groove, said second wheel having a continuous tongue matingly connecting with said groove, said cord being movable through said groove of said squeezing roller assembly, said tongue and said groove applying squeezing pressure against said cord compressing said cord to evenly distribute said liquid medium within said cord and for removing excess said liquid medium from said cord;
   a first drying means, said cord to be moved through said first drying means after passage through said squeezing roller assembly; and
   a wind-up drum, said cord to be moved onto said wind-up drum and retained thereon.

2. The cord impregnator as defined in claim 1 wherein:
   a vacuum source connected to said squeezing roller assembly, said vacuum source functioning to remove said liquid medium that is squeezed from said cord by said squeezing roller assembly, said vacuum source including a series of spoke-like conduits formed within said first wheel, a vacuum is to be drawn into said conduits, said conduits connecting with said groove, the excess liquid medium flowing from said groove into said conduits due to the force of said vacuum.

3. The cord impregnator as defined in claim 2 wherein:
   said first drying means comprising a combination heater and air blower, said cord impregnator including second drying means, said second drying means connected to said wind-up drum, said second drying means moving heated air across the periphery of said drum as said cord is being wound on said wind-up drum.

* * * * *